(12) United States Patent
Lesti et al.

(10) Patent No.: US 10,070,979 B2
(45) Date of Patent: Sep. 11, 2018

(54) DEVICE FOR EXPLORABLE STOMACH GASTRIC BYPASS

(71) Applicant: Francesco Lesti, Chieti (IT)

(72) Inventors: Giovanni Lesti, Chieti (IT); Urbano Barbabella, Accumoli (IT)

(73) Assignee: Francesco Lesti, Chieti (IT)

( * ) Notice: Subject to any disclaimer, the term of this patent is extended or adjusted under 35 U.S.C. 154(b) by 55 days.

(21) Appl. No.: 14/910,678

(22) PCT Filed: Aug. 1, 2014

(86) PCT No.: PCT/IB2014/063618
§ 371 (c)(1),
(2) Date: Feb. 5, 2016

(87) PCT Pub. No.: WO2015/019259
PCT Pub. Date: Feb. 12, 2015

(65) Prior Publication Data
US 2016/0193062 A1 Jul. 7, 2016

(30) Foreign Application Priority Data

Aug. 5, 2013 (IT) .............................. RM2013A0460

(51) Int. Cl.
*A61F 2/04* (2013.01)
*A61F 5/00* (2006.01)

(52) U.S. Cl.
CPC ............ *A61F 5/0063* (2013.01); *A61F 5/005* (2013.01)

(58) Field of Classification Search
CPC ............................... A61F 5/005; A61F 5/0063
See application file for complete search history.

(56) References Cited

U.S. PATENT DOCUMENTS

| 4,592,339 | A | 6/1986 | Kuzmak et al. |
| 4,696,288 | A | 9/1987 | Kuzmak et al. |
| 2004/0133219 | A1 | 7/2004 | Forsell |
| 2005/0154274 | A1 | 7/2005 | Jarsaillon et al. |
| 2008/0183196 | A1 | 7/2008 | Jarsaillon et al. |
| 2009/0062824 | A1 | 3/2009 | Berg et al. |
| 2010/0305397 | A1* | 12/2010 | Birk ........................ A61F 5/005 600/37 |

(Continued)

FOREIGN PATENT DOCUMENTS

| WO | 03/057090 | 7/2003 |
| WO | 2004/010910 | 2/2004 |

OTHER PUBLICATIONS

International Search Report for PCT/IB2014/063618, dated Jan. 5, 2015, four pages.

(Continued)

*Primary Examiner* — Thaddeus Cox
(74) *Attorney, Agent, or Firm* — Nixon & Vanderhye P.C.

(57) ABSTRACT

The present invention relates to a device for implementing an explorable stomach gastric bypass apt to be implanted in a patient who needs it. In particular, such device comprises a main body having at least one elastic portion made of silicone material and a covering element of the main body itself that in turn comprises an extensible portion. The extensible portion is positioned at the elastic portion and characterizes in that it comprises an excess of material compared to the size of the elastic portion itself.

13 Claims, 3 Drawing Sheets

(56) References Cited

U.S. PATENT DOCUMENTS

| | | | |
|---|---|---|---|
| 2010/0312047 A1* | 12/2010 | Forsell | A61B 17/0469 600/37 |
| 2013/0296900 A1* | 11/2013 | Szewczyk | A61F 5/0063 606/157 |
| 2014/0257033 A1* | 9/2014 | Frering | A61F 5/003 600/37 |

OTHER PUBLICATIONS

Written Opinion of the ISA for PCT/IB2014/063618, dated Jan. 5, 2015, five pages.
Int'l Preliminary Report on Patentability for PCT/IB2014/063618, dated Sep. 8, 2015, 15 pages.

* cited by examiner

DEVICE FOR EXPLORABLE STOMACH GASTRIC BYPASS

This application is the U.S. national phase of International Application No. PCT/IB2014/063618, filed 1 Aug. 2015, which designated the U.S. and claims priority to Italian Application No. RM2013A000460, filed 5 Aug. 2013; the entire contents of each of which are hereby incorporated by reference.

TECHNICAL FIELD OF THE INVENTION

The present invention relates to a device necessary for implementing an explorable gastric bypass apt to be implanted in a patient who needs it. In particular, such device comprises a main body having at least one elastic portion made of silicone material and a covering element of the main body itself which in turn comprises an extensible portion. The extensible portion is positioned at the elastic portion and characterizes in that it comprises an excess of material compared to the size of the elastic portion itself.

STATE OF KNOWN ART

Most part of bariatric surgeons believes that the gastric bypass operation is the ideal operation for treating severe obesity. In particular, such operation consists in creating a gastric pocket which is placed in communication with a jejunal loop in order to avoid the passage of the alimentary bolus and therefore of the alimentary liquids into the stomach and in the duodenum (Roux-en-Y Gastric Bypass—RYGBP).

Several studies assert the efficiency of the method in seriously obese subjects.

However, a series of problems has appeared relating the surgical technique for obtaining the gastric task. In particular, the stomach portion excluded from the passage of the bolus and the alimentary liquids actually remains inaccessible to any endoscopic scanning. The main disadvantage linked to the isolation of the residue stomach portion is the missed possibility of diagnosing and treating pathologies which in case develop at the expense of the stomach or however of the duodenum and the main biliary route (MBR). For example, the stomach cancer is still an important death cause in the western world. Currently the number of endoscopic processes, performed for the diagnose and therapy of the benign and malign diseases, of the stomach of MBR and pancreas, is so that the fact of allowing the scanning thereof even in individuals subjected to gastric bypass remains of fundamental medical importance. It is reminded that in the world more than 100,000 operation/year of gastric bypasses are performed every year for serious obesity and for other metabolic diseases.

In particular, an attempt of solving the above-illustrated problem was proposed by means of developing a method of laparoscopic gastric bypass with fundectomy and explorable residue stomach LRYGBP (fse) implemented by the author of the present invention and shown for the first time to the world congress of the IFSO (International Federation of Surgical obesity) in São Paulo in Brazil (August 2002).

In particular, with such method in the first 50 cases a passage was created between the gastric pocket and the stomach remaining excluded, passage constituted by a channel of about 2 cm closed with an adjustable gastric bandage which should have the purpose not only of closing the passage to the bole and the alimentary liquids but even of adjusting the quantity under particular conditions, such as pregnancy, chemotherapy or other needs. However, it was observed that the use of adjustable bandages, necessarily made of elastic material, was accompanied by a migration of the bandage through the created gastro-jejunal anastomosis. In particular, as shown by Lesti et al. on a sample of 50 patients subjected to gastric bypass with fundectomy and explorable stomach and with closing of the gastric tubule with an adjustable gastric bandage, in 5 cases the migration of the bandage in the stomach remaining excluded or in the jejunum through the anastomosis was observed (JW-MGreve, F Furbetta, G Lesti, R A Weiner, J M Zimmerman, L Angrisani Obesity Surgery 2005).

For this reason, the elastic explorable gastric bandage was subsequently replaced by a tract made of Gore-Tex in polytetrafluoroethylene of 1×7 cm and thickness of 1 mm. However, the polytetrafluoroethylene, even if it characterizes for a perfect compatibility with the biological tissues, as it is inelastic, has the disadvantage of a closing which can be hardly overcome by the endoscopic probe. In fact, if the tracts made of Gore-Tex made possible to solve the problem of the migration of the gastric bandage, on the other side, as they are not elastic, they do not allow to obtain an efficient closing, after the passage of the endoscopic probe, of the hole which puts into communication the gastric pocket with the stomach remaining excluded.

In the light of what described it appears obvious the need of being able to have available an operative solution allowing to scan with diagnostic and/or operative possibilities of the remaining excluded stomach, at the same time guaranteeing the concrete deviation of the bole and of the alimentary liquids directly from the gastric pocket to the jejunal loop formed during the surgical operation.

The object of the present invention is to propose a new and original solution to the disadvantages existing in the state of known art.

SUMMARY OF THE INVENTION

In particular, the present description relates, as already shown, to a device for the gastric bypass characterizing in that it allows, on one side, to create a classical gastric pocket of 30 cc, actually excluding the stomach to the passage of the alimentary bolus and, on the other side, to allow the scanning with diagnostic and/or operative possibilities of the stomach remaining excluded by means, for example, of using endoscopic probes.

In particular, such result is obtained by means of implementing a device for the explorable gastric bypass comprising at least one elastic portion made of silicone material coated with a covering element which in turns comprises an extensible portion along the direction of longitudinal development of the device and made of biocompatible but not elastic material. In the specific case, the extensible portion is made in this way thanks to the presence of an excess of material compared to the real sizes of the elastic portion to be coated.

The main advantage of the above-described, and better detailed hereinafter, conformation consists in that it is possible increasing the length of the device in reversible way, thus allowing to be able to come back to the starting sizes without an alteration of the form/structure of the device itself being present.

Advantageously, then, the device of the invention allows being able to perform successfully a gastric bypass operation and to access, when needed, to the gastric lumen remaining excluded, by promoting the prevention and/or the diagnosis and/or the treatment of pathologies at the expense of the stomach or however of the duodenum and of the main biliary route. Furthermore, as demonstrated by the inventors of the present invention, the device of the invention allows reducing significantly the migration of the same through the gastric-jejunal anastomosis, migration which instead is observed with the use of the adjustable or not adjustable gastric bandages, currently known and in use in the obesity surgery (bariatric surgery).

Furthermore, the device of the invention, thanks to the structural features defining it and detailed hereinafter, results to be easily positionable in the operation seat, by demonstrating a great use practicality and handling useful to the surgeon.

Therefore the object of the present invention is a device for the gastric bypass as defined in the independent claim 1.

Preferred features of the object of the present description are reported in the depending claims.

Additional advantages, as well as the features and the use modes of the present invention, will result evident from the following detailed description related to its possible embodiments, shown by way of example and not with limitative purpose.

DETAILED DESCRIPTION OF THE INVENTION

Figure 1:
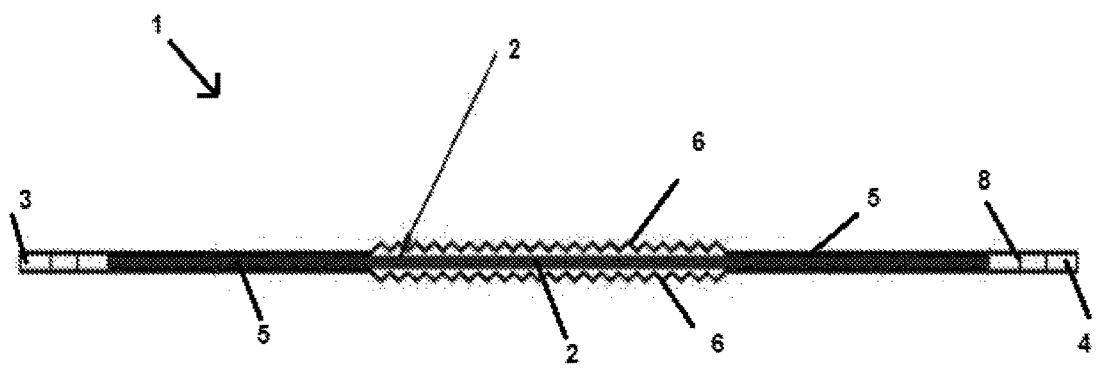
FIG. 1 shows a scheme of an embodiment of the device of the invention.

The present description relates to a device 1 for carrying out an explorable gastric bypass with excluded stomach apt to be implanted in a patient who needs it (FIG. 1).

In particular, under the term gastric bypass in the present description a technique of bariatric surgery is meant, substantially consisting in creating a gastric pocket which is connected to a jejunal loop in order to avoid the passage of the bolus and the alimentary liquids in the stomach and the duodenum.

The device 1 of the invention actually is a medical device suitable to create a gastric pocket in a method of gastric bypass with explorable stomach. In particular, as shown in FIG. 1, the device comprises a main body 2 an a covering element 5 of the main body itself 2.

The main body 2, as shown in FIGS. 1-4, has a mainly longitudinal development wherein a first end 3 and a second end 4 can be distinguished. The length of the main body 2, and therefore of the device 1, could vary depending upon the operating needs of the surgeon performing the gastric bypass with explorable stomach such as, for example, the width of the stomach walls and the quantity and thickness of the adjacent fat. Preferably, the main body 2 has a longitudinal development of 120 mm.

The main body 2 comprises at least an elastic portion made of silicone material. Preferably, the elastic portion mainly constitutes the central portion of the device 1. In a preferred embodiment of the invention, the main body 2 is entirely made of silicone material. By way of example and not with limitative purpose, the silicone material thereof the elastic portion is partially or entirely made, can be implantable USP Class VI and/or ISO 10993 the features of physiologically inert material thereof allow the biocompatibility with biological tissues.

In an embodiment of the invention the silicone material has a modulus of elasticity between 130-170 GPa. In other words, the device 1 could comprise at least an elastic portion with a modulus elasticity of 130, 135, 140, 145, 150, 155, 160, 170 GPa. In particular, the silicone material with such range of elasticity demonstrated to be particularly suitable to guarantee the passage of an endoscopic probe by exerting a minimum pressure by the operator and, on the other side, the re-activation of the orifice closing after extracting the probe itself.

The main body 2 is coated with a covering element 5, preferably made of biocompatible material, which is integral thereto at least at two ends 3 and 4. In particular, the covering element 5 comprises an extensible portion 6 along the direction of longitudinal development of the device 1 and positioned at the elastic portion of the main body 2, as shown by way of example in FIG. 1. Such extensible portion is made of biocompatible and not elastic material. In the specific case, the portion 6 is made extensible due to the fact that it comprises excess material compared to that needed to coat the entire elastic portion of the main body 2. In other words, then, the extensible portion 6 comprises a greater quantity of material than that needed to coat the elastic portion. By way of example and not with limitative purpose, the extensible portion 6 could have folds, be pre-formed, for example, like an accordion as schematically represented in FIG. 1.

In a preferred embodiment of the present invention the covering element 5 comprises or is made of polytetrafluoroethylene.

Figure 2A:
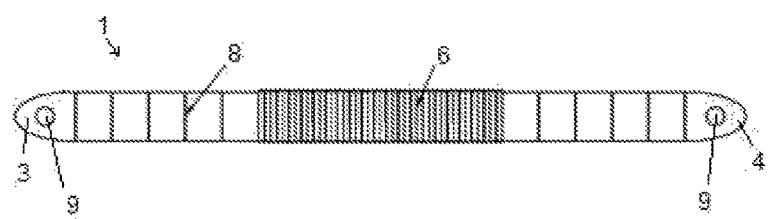
FIGS. 2A and 2B show an embodiment of the device of the invention in a not operative position.
Figure 2B:
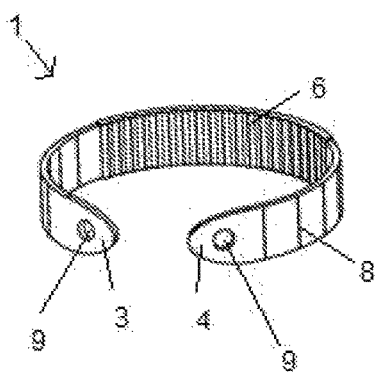

As shown in FIGS. 2A and 2B, the device 1 can be present in a first not operative conformation/position in which the first end 3 and the second end 4 are not in contact with each other. As it is clear from the figures, in said first position the device 1 actually is an open system in which the two ends 3, 4 are in continuity only on one side thereof. In an embodiment of the invention, the length of the device 1 in said first position is about 120 mm.

Alternatively, the device 1 can be positioned according to an operative conformation in which the first end 3 and the second end 4 are in contact. In other words, in such second position the device forms a closed system as sketched in FIGS. 3 and 4.

In particular, during the surgical operation of gastric bypass with explorable stomach, the positioning of the device 1 below the gastro-jejunual anastomosis and the passage from the first not operative position to the second operative position will allow creating the gastric pocket, by delimiting the same.

In order to allow the positioning of the device 1 according to the operative conformation, the first end 3 and the second end 4 can comprise positioning means. Under positioning means in the present invention means are meant suitable to allow a preferably stable and long lasting contact between the two ends 3, 4. By purely way of example and not with limitative purpose, such positioning means can comprise tongue-and-groove systems.

In the embodiment in which the device 1 has no positioning means, the second operative position can be however obtained by stitching the two ends 3, 4, for example, by using a surgical linear stitching machine or a not re-absorbable metallic clip.

Furthermore, in order to favour the surgeon in closing the device 1, the first end 3 and the second end 4, as shown in FIGS. 2A and 2B, can be equipped with holes 9 for the passage of threads or surgical instruments facilitating the traction of the device 1.

Figure 4:
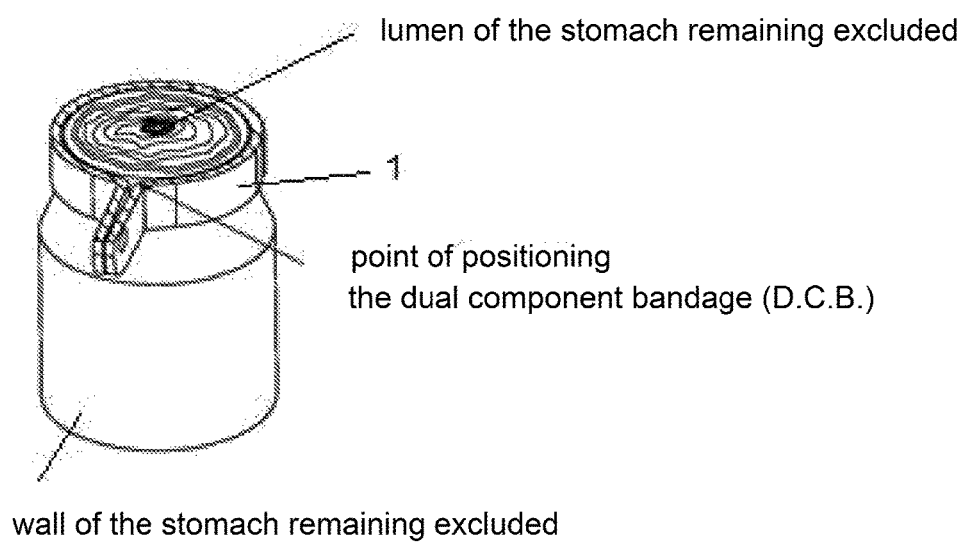
FIG. 4 shows an embodiment of the herein described device wherein the point of positioning the Dual Component Bandage (D.C.B) of the invention is represented.

Preferably, when the device 1 is in the operative position, it forms a closed system with a substantially circular conformation, whose minimum diameter is comprised between 15-18 mm. Operatively, such minimum diameter characterizes the device 1 in the operative conformation in absence of endoscopic probes or other surgical/diagnostic instruments inside the gastric lumen, as shown in FIG. 4.

As already mentioned above, the device 1 of the invention, allows being able to perform successfully an operation of gastric bypass with stomach remaining excluded with diagnostic and/or operative possibilities. Therefore, when the device is in said operative position, it allows the passage of an endoscopic probe thanks to the fact that the main body 2 comprises an elastic portion the extension thereof can be followed by the covering element 5 which comprises an extensible portion 6. In this regard, for example, after the insertion of an endoscopic probe, a lengthening of the device 1 can be provided and, in particular, a lengthening of the elastic portion of the main body by 25% with respect to the length of the device 1 in the operative conformation established by the surgeon as suitable, for a given patient, to prevent the passage of the alimentary bolus in the stomach remaining excluded.

In an embodiment, in presence of an endoscopic probe or however any other instrument considered suitable to perform a scanning for diagnostic and/or operative purposes of the stomach remaining excluded, the closed conformation substantially with circular shape of the device 1 can reach a maximum diameter between 22-25 mm.

Furthermore, the device 1 can even comprise reference elements 8 apt to signal to the surgeon the points of potential contact between said first and second end 3, 4. In other words, the presence of said reference elements 8 allows varying the diameter of the circular closed conformation (device in the operative position) during implant.

In particular, such reference points 8 favour the positioning of the device 1 in the operative position. In an embodiment of the invention said reference elements 8 are spaced by 5 mm. By way of example, as shown in FIGS. 1-4, such reference elements 8 can be shaped like notches or lines perpendicular to the longitudinal axis of the device 1, in case with different colours. By way of example and not with limitative purpose, the reference elements 8 can be provided under the form of two outer notches, each one on each end 3 or 4, at a distance of about 100 mm, two inner notches spaced apart by about 40 mm, and pairs of intermediate notches spaced apart each one by 50, 60, 70, 80, 90 mm.

The device of the invention can be implemented with any technique considered suitable by the person skilled in the art. By way of example and not with limitative purpose, the device 1 can be implemented by RTV (Room Temperature Vulcanisation) or HTV (High Temperature Vulcanisation) printing and vulcanisation in a single body and a single size.

Herein even a surgical method for carrying out a gastric bypass with explorable stomach remaining excluded using the device 1 of the invention is also described. In particular, such surgical method of gastric bypass with explorable stomach remaining excluded characterizes for a series of operative passages thereamong a passage of positioning the device 1 below the gastro-jejeunal anastomosis and closing the same in an operative conformation in a way analogous to what already described above.

Preferably the device 1 will be positioned at about 1-2 cm below the gastro-jejeunal anastomosis which has its cranial apex at about 2-3 cm from the cardia. In particular, then in an embodiment of the here described surgical method a gastric pocket with the sizes of about 5×3 cm and a capacity of about 30 ml is created.

The method could further comprise a passage of removing the gastric bottom portion. Advantageously, the removal of the gastric bottom portion is associated to a not secretion of the orectic ghrelin hormone with consequent appetite decrease of the patient.

In an embodiment, the above method is implemented by means of laparoscopy.

Mode of Implanting an Embodiment of the Device 1

Figure 3A:
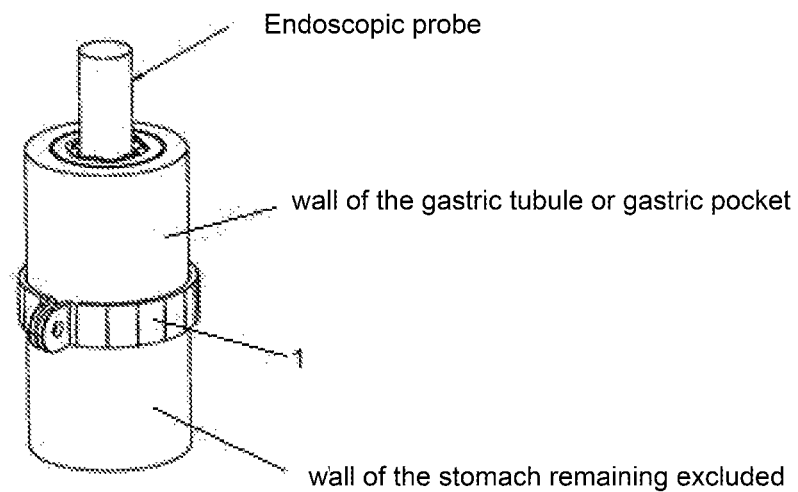
FIGS. 3A and 3B show in schematic form an embodiment of the device of the invention in an operative position, in presence and absence of an endoscopic probe respectively.
Figure 3B:
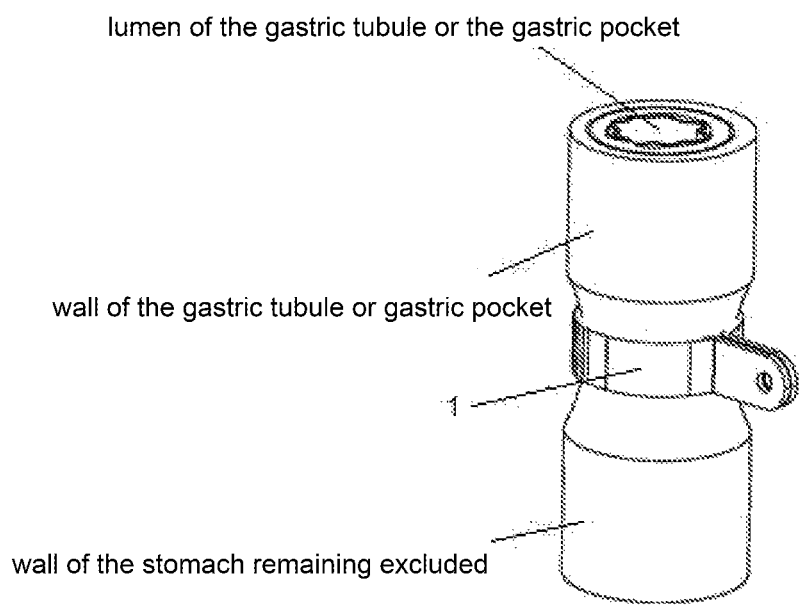

The device 1 with its coating made of PTFE (polytetrafluoroethylene) is passed under the gastric tubule, containing inside a gastric probe with a diameter of 12 mm, and grasped at the two ends, preferably shaped like a semi-ellipse for an easy grasp, and then pulled upwards with a thread passing forceps inserted in the suitable small holes 9 with diameter of about 3 mm existing at the ends. At this point a Johan forceps grasps the device, following the reference elements 8 and closes it around the gastric tubule without exerting any pressure. This is then the co-called outer opening circumference of the neo-gastric tubule with the inserted probe (C.A.) (FIG. 3A). At this point, depending upon the C.A. size obtained by the corresponding reference elements 8, the surgeon, once the gastric probe is made to be withdrawn by the anaesthetist, will pull the device 1 so that in the definite closing it scales down by four reference elements 8 inwards, by obtaining in this way an outer closing circumference (C.C.) smaller by 40 mm than the opening one. The 40 mm shortening of the circumference is determined by 30 mm corresponding to the gauge of the gastric probe and by 10 mm needed to the silicone lengthening to exert an adequate closing of the gastric tubule). The final length of the device 1 in its closed operative conformation (C.C.) usually varied from 50 to 70 mm with a minimum diameter of 15-18 mm and a maximum diameter of 22-25 mm.

The silicone compression elastic force, after shortening by 10 mm, is related to a lengthening of about 25% in the extensible area needed to occlude the gastric lumen below the anastomosis in the point of applying the device 1 so as to prevent the passage of the liquids and/or the alimentary bolus from the gastric pocket to the gastric cavity.

The device, during implant, can be closed with a metallic clip or even better with a stroke of linear stitching machine.

The present invention has been so far described by referring to the preferred embodiments thereof. It is to be means that other embodiments belonging to the same inventive core may exist, all belonging to the protection scope of the here-below reported claims.

The invention claimed is:

1. A device for carrying out an explorable stomach gastric bypass apt to be implanted in a patient comprising:
   a main body having a first end and a second end, said main body comprising at least one elastic portion made of silicone material, and
   a covering element of said main body comprising an extensible portion along a direction of longitudinal development of the device and positioned at said elastic portion, said extensible portion comprising an excess of material compared to that needed to coat the entire elastic portion;
   wherein said device is extensible in a reversible way either when in use or not in use, and wherein said silicone material has a modulus of elasticity between 130-170 GPa.

2. The device according to claim 1, wherein said first end and said second end comprise positioning means.

3. The device according to claim 1, wherein said device is positionable:
in a first non-operative position in which said first end and said second end are not in contact with each other, and
in a second operating position in which said first end and said second end are placed in contact with each other in such a manner that said device has a substantially circular closed conformation.

4. The device according to claim 3, wherein said device in said first non-operating position has a length of 120 mm.

5. The device according to claim 3, wherein when said device is in said second operative position, said circular closed conformation has a minimum diameter between 15 mm and 18 mm.

6. The device according to claim 3, wherein when in said second operative position the device lets an endoscopic probe pass through thus allowing said conformation to reach a maximum diameter between 22 mm and 25 mm.

7. The device according to claim 1, wherein said device comprises reference elements adapted to indicate points of contact between said first end and said second end in order to position said device in said second operative position.

8. The device according to claim 7, wherein said reference elements are spaced apart from each other along the direction of longitudinal development of the device by 5 mm.

9. The device according to claim 1, wherein said extensible portion has folds.

10. The device according to claim 1, wherein said main body is entirely made of silicone material.

11. The device according to claim 1, wherein said covering element comprises polytetrafluoroethylene.

12. A surgical method for carrying out a gastric bypass in a patient, with explorable stomach remaining excluded, comprising a step of positioning a device below a gastro-jejeunal anastomosis and closing said device in an operative conformation; said device comprising:
a main body having a first end and a second end, said main body comprising at least one elastic portion made of silicone material, and
a covering element of said main body comprising an extensible portion along a direction of longitudinal development of the device and positioned at said elastic portion, said extensible portion comprising an excess of material compared to that needed to coat the entire elastic portion;
wherein said device is extensible in a reversible way either when in use or not in use.

13. The method according to claim 12, wherein said silicone material has a modulus of elasticity between 130-170 GPa.

* * * * *